United States Patent [19]

Bright

[11] 4,098,994

[45] Jul. 4, 1978

[54] SULFAMIDE DERIVATIVES OF 4-DEOXY-OLEANDOMYCIN

[75] Inventor: Gene M. Bright, Groton, Conn.

[73] Assignee: Pfizer Inc., New York, N.Y.

[21] Appl. No.: 833,405

[22] Filed: Sep. 15, 1977

[51] Int. Cl.² .................. C07H 17/08; A01N 9/00
[52] U.S. Cl. .................... 536/9; 424/180; 536/17
[58] Field of Search ........................... 536/9

[56] References Cited

U.S. PATENT DOCUMENTS 4,036,853  8/1977  Sciavolino ............... 536/9
4,069,379  1/1978  Sciavolino ............... 536/9

Primary Examiner—Johnnie R. Brown
Assistant Examiner—Blondel Hazel
Attorney, Agent, or Firm—Francis X. Murphy; Charles J. Knuth; Albert E. Frost

[57] ABSTRACT

This invention relates to novel antibacterial agents and, in particular, to 11-alkanoyl-4''-deoxy-4''-sulfamide-oleandomycins. Synthesis of these new agents is carried out by treatment of an 11-alkanoyl-4''-deoxy-4''-amino-oleandomycin with a substituted aminosulfonyl chloride or azide.

7 Claims, No Drawings

SULFAMIDE DERIVATIVES OF 4″-DEOXY-OLEANDOMYCIN

BACKGROUND OF THE INVENTION

1. Field of the Invention

This invention relates to a series of 11-alkanoyl-4″-deoxy-4″-sulfamide-oleandomycins and their pharmaceutically acceptable acid addition salts, which are useful as antibacterial agents.

2. Description of the Prior Art

Oleandomycin, its production in fermentation broths and its use as an antibacterial agent, was first described in U.S. Pat. No. 2,757,123. The naturally occurring compound is known to have the following structure:

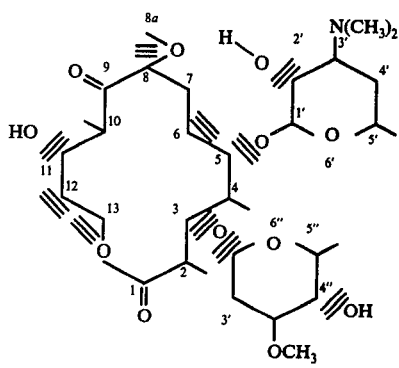

The conventionally accepted numbering scheme and stereochemical representation for oleandomycin and similar compounds is shown at a variety of positions.

Several synthetic modifications of this compound are known, particularly those in which from one to three of the free hydroxyl groups found at the 2′, 4″ and 11-positions are esterified as acetyl esters. In addition, there are described in U.S. Pat. No. 3,022,219 similar modifications in which the acetyl in the above-mentioned esters is replaced with another, preferably unbranched lower alkanoyl of three to six carbon atoms.

SUMMARY OF THE INVENTION

The semi-synthetic oleandomycin compounds of this invention are of the formula:

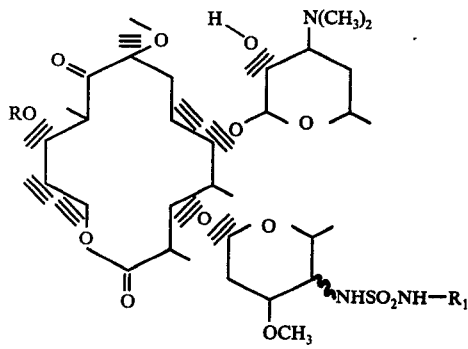

and a pharmaceutically acceptable acid addition salt thereof wherein R is alkanoyl having from two to three carbon atoms; and $R_1$ is selected from the group consisting of alkyl having from one to four carbon atoms, phenyl and substituted phenyl wherein said substituent is selected from the group consisting of methyl, methoxy, chloro, fluoro and trifluoromethyl.

Preferred as antibacterial agents are the compounds wherein $R_1$ is said substituted phenyl. Within this group N-(11-acetyl-4″-deoxy-4″-oleandomycyl)-N′-(p-methoxyphenyl)-sulfamide, N-(11-acetyl-4″-deoxy-4″-oleandomycyl)-N′-(p-chlorophenyl)sulfamide and N-(11-acetyl-4″-deoxy-4″-oleandomycyl)-N′-(p-tolyl)sulfamide are especially preferred. Also preferred are those compounds wherein $R_1$ is said alkyl. Especially preferred in this group is N-(11-acetyl-4″-deoxy-4″-oleandomycyl)-N′-methylsulfamide.

The stereochemistry of the starting materials leading to the antibacterial agents of the present invention is that of the natural material. Oxidation of the 4″-position of the natural oleandomycin derivatives leads to the 4″-ketone. Reductive amination of the 4″-oxo compounds presents an opportunity for the stereochemistry of the 4″-amino group to be different from the natural product. The absolute stereochemistry of the 4″-amino group and the 4″-sulfamide, for which the amine is a starting material, has not yet been established.

DETAILED DESCRIPTION OF THE INVENTION

In accordance with the process for synthesizing the 11-alkanoyl-4″-deoxy-4″-sulfamide-oleandomycin antibacterials related to 1, the following scheme is illustrative:

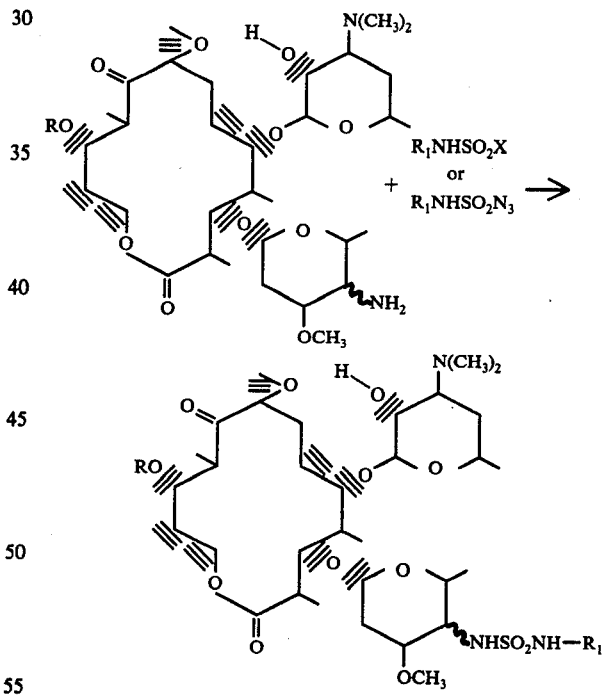

wherein R and $R_1$ are as previously indicated, and X is chloro or bromo.

Acylation of the 4″-amino moiety is effected using an alkyl- or arylaminosulfonyl azide prepared according to the procedure of Shozda, et al., J. Org. Chem., 32, 2876 (1967). Equally applicable to the synthesis of the instantly claimed compounds is the acylation of the aforementioned 4″-amino compound with an alkyl- or arylaminosulfonyl halide, such as the sulfonyl chloride. The aminosulfonyl chloride reagents are prepared by literature procedures, such as taught by Matier, et al., J. Med. Chem., 15, 538 (1972).

Experimentally, one mole of the 11-alkanoyl-4"-deoxy-4"-aminooleandomycin is contacted with at least one mole, and as much as a two fold excess, of the appropriate aminosulfonyl halide or azide in a reaction inert solvent containing about 2 to 4 moles of a tertiary amine, such as triethylamine. The order of addition is not critical, but it is preferred that the halide or azide be added to a solution of the 11-alkanoyl-4"-deoxy-4"-amino-oleandomycin and the tertiary amine in the reaction inert solvent.

The solvent employed should appreciably solubilize the reactants and not react to any extent with the reagents or the reaction product. Preferred as solvents are those which are polar, aprotic and liquids at ice-bath temperatures. Such solvents include chlorinated hydrocarbons, alkylnitriles and ethers. Especially preferred as a solvent is methylene chloride.

The reaction time and temperature are not critical parameters. It is preferred that a reaction temperature of 0°–25° C. be employed during the reaction period. At these temperatures the reaction is concluded in about two to four hours.

Following the completion of the reaction, the solvent is removed under reduced pressure, and the residual product chromatographed on a silica gel packed column. The product is conveniently eluted from the column using acetone or a mixture of acetone-methanol. The fractions are monitored for the product using thin-layer chromatography. Those fractions containing the pure product are subsequently combined and concentrated in vacuo to dryness.

The starting 4"-amino compounds used in the synthesis of the antibacterial agents of the present invention are synthesized by oxidation of the natural oleandomycin followed by a reductive amination of the ketone as hereinafter described.

In the utilization of the chemotherapeutic activity of those compounds of the present invention which form salts, it is preferred, of course, to use pharmaceutically acceptable salts. Although water-insolubility, high toxicity or lack of crystalline nature may make some particular salt species unsuitable or less desirable for use as such in a given pharmaceutical application, the water insoluble or toxic salts can be converted to the corresponding pharmaceutically acceptable bases by decomposition of the salt, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

The novel 4"-deoxy-4"-sulfamide-oleandomycin derivatives described herein exhibit in vitro activity against a variety of Gram-positive microorganisms such as *Staphylococcus aureus* and *Streptococcus pyogenes* and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sick room utensils; and as industrial antimicrobials, for example, in water treatment, slime control, paint and wood preservation.

For in vitro use, e.g., for topical application, it will often be convenient to compound the selected product with a pharmaceutically acceptable carrier such as vegetable or mineral oil or an emollient cream. Similarly, they may be dissolved or dispersed in liquid carriers or solvents, such as water, alcohol, glycols or mixtures thereof or other pharmaceutically acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Grampositive microorganisms via the oral and/or parenteral routes of administration in animals, including man. Their in vivo activity is more limited as regards susceptible organisms and is determined by the usual procedure which comprises mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests ae simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 5 mg./kg. to about 200 mg./kg. of body weight per day. The favored dosage range is from about 25 mg./kg. to about 100 mg./kg. of body weight per day and the preferred range from about 50 mg./kg. to about 75 mg./kg. of body weight per day. Vehicles suitable for parenteral injection may be either aqueous such as water, isotonic saline, isotonic dextrose, Ringer's solution, or non-aqueous such as fatty oils or vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE 1

N-(11-Acetyl-4''-deoxy-4''-oleandomycyl)-N'-methylsulfamide

To 50 ml. of dry methylene chloride containing 2.0 g. (2.7 mmoles) of 11-acetyl-4''-deoxy-4''-amino-oleandomycin and 1.13 ml. (8.1 mmoles) of triethylamine and cooled to 0° C. is added 350 mg. (2.7 mmoles) of methylaminosulfonyl chloride in 1.0 ml. of dry methylene chloride. After stirring for one hour at 0° C. an additional 350 mg. of methylaminosulfonyl chloride is added over a period of 30 minutes. At the end of the addition the reaction mixture is allowed to stir for 30 minutes and the solvent is then removed in vacuo. The residual product is chromatographed on a silica gel packed 3.5 × 40 cm. column using acetone-methanol (9:1, v:v) as the eluate. Concentration of the combined fractions gives 800 mg. of the desired product.

NMR ($\delta$, $CDCl_3$): 2.08 (3H)s; 2.30 (6H)s; 2.6–2.82 (5H)m; and 3.52 (3H)s.

EXAMPLE 2

Starting with the appropriate alkylaminosulfonyl chloride and 4''-amino-oleandomycin and employing the procedure of Example 1, the following compounds are prepared:

N-(11-acetyl-4''-deoxy-4''-oleandomycyl)-N'-ethylsulfamide; N-(11-acetyl-4''-deoxy-4''-oleandomycyl)-N'-(i-propyl)sulfamide; N-(11-acetyl-4''-deoxy-4''-oleandomycyl)-N'-(t-butyl)sulfamide; N-(11-acetyl-4''-deoxy-4''-oleandomycyl)-N'-(s-butyl)sulfamide; N-(11-propionyl-4''-deoxy-4''-oleandomycyl)-N'-(n-propyl)sulfamide; N-(11-propionyl-4''-deoxy-4''-oleandomycyl)-N'-(n-butyl)sulfamide; and N-(11-propionyl-4''-deoxy-4''-oleandomycyl)-N'-(t-butyl)sulfamide.

EXAMPLE 3

N-(11-Acetyl-4''-deoxy-4''-oleandomycyl)-N'-(p-tolyl)sulfamide

To a solution of 2.0 g. (2.75 mmoles) of 11-acetyl-4''-deoxy-4''-aminooleandomycin and 1.4 ml. (10 mmoles) of triethylamine in 30 ml. of dry methylene chloride at ambient temperatures is added 5 drops of p-methylphenylaminosulfonyl azide. After stirring for 10 minutes the reaction mixture is examined by thin-layer chromatography to determine the presence of any oleandomycin starting material. Additional azide is added in one drop increments until there is no remaining starting oleandomycin.

The solvent is removed under reduced pressure and the residual product is chromatographed on a silica gel packed 4 × 40 cm. column using acetone as the eluate. The fractions containing the product are combined and concentrated to give 1.46 g. of a colorless amorphous solid.

NMR ($\delta$, $CDCl_3$): 2.03 (3H)s; 2.30 (3H)s; 2.39 (6H)s; 2.63 (2H)m; 3.43 (3H)s; and 7.12 (4H)s.

EXAMPLE 4

The procedure of Example 3 is repeated, starting with the requisite reagents, to give the following analogs:

N-(11-acetyl-4''-deoxy-4''-oleandomycyl)-N'-phenylsulfamide; N-(11-propionyl-4''-deoxy-4''-oleandomycyl)-N'-phenylsulfamide; N-(11-acetyl-4''-deoxy-4''-oleandomycyl)-N'-(o-tolyl)sulfamide; N-(11-acetyl-4''-deoxy-4''-oleandomycyl)N'-(m-tolyl)sulfamide; N-(11-propionyl-4''-deoxy-4''-oleandomycyl)-N'-(p-tolyl)sulfamide; and N-(11-propionyl-4''-deoxy-4''-oleandomycyl)-N'-(m-tolyl)sulfamide.

EXAMPLE 5

N-(11-Acetyl-4''-deoxy-4''-oleandomycyl)-N'-(p-methoxyphenyl)sulfamide

The procedure of Example 3 is again repeated, starting with 2.0 g. (2.75 mmoles) of 11-acetyl-4''-amino-oleandomycin, 1.4 ml. of triethylamine, 5 drops of p-methoxyphenylaminosulfonyl azide and 30 ml. of dry methylene chloride to give, after chromatographing, 850 mg. of the desired product.

NMR ($\delta$, $CDCl_3$): 2.09 (3H)s; 2.46 (6H)s; 2.65 (2H)m; 3.46 (3H)s; 3.81 (3H)s; 6.85 and 7.21 (4H).

EXAMPLE 6

Following the procedure of Example 3, and starting with the appropriate azide and amine, the indicated products are formed:

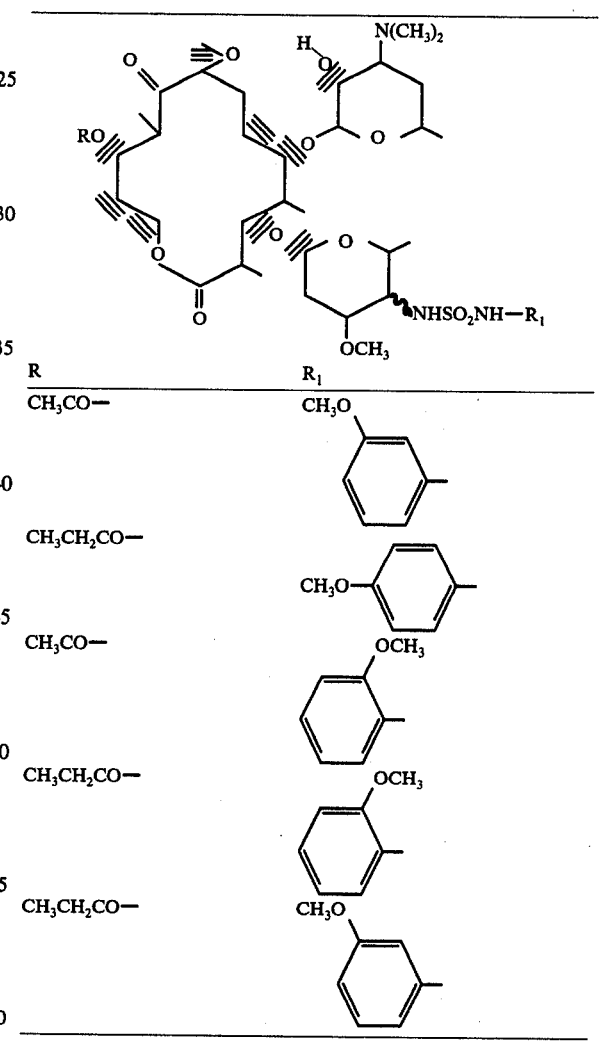

| R | $R_1$ |
|---|---|
| $CH_3CO-$ | $CH_3O-$ |
| | $CH_3O-\phenyl-$ |
| $CH_3CH_2CO-$ | $CH_3O-\phenyl-$ |
| $CH_3CO-$ | $\phenyl-OCH_3$ |
| $CH_3CH_2CO-$ | $\phenyl-OCH_3$ |
| $CH_3CH_2CO-$ | $CH_3O-\phenyl-$ |

EXAMPLE 7

N-(11-Acetyl-4''-deoxy-4''-oleandomycyl)-N'-(p-chlorophenyl)sulfamide

To a solution of 2.0 g. (2.75 mmoles) of 11-acetyl-4''-deoxy-4''-aminooleandomycin and 1.4 ml. of triethylamine in 35 ml. of dry methylene chloride is added sufficient p-chlorophenylaminosulfonyl azide that after 10 minutes of stirring all the starting amine has been utilized. The reaction mixture is concentrated to a foam and the residual material chromatographed over silica gel, using acetone as the eluate. The fractions containing the product are combined and concentrated to dryness to give 740 mg. of a colorless solid.

NMR (δ, CDCl₃): 2.05 (3H)s; 2.57 (6H)s; 2.63 (2H)m; 3.38 (3H)s; and 7.18 (4H)s.

EXAMPLE 8

Starting with the appropriate amine and requisite azide, and employing the procedure of Example 7, the following compounds are synthesized:

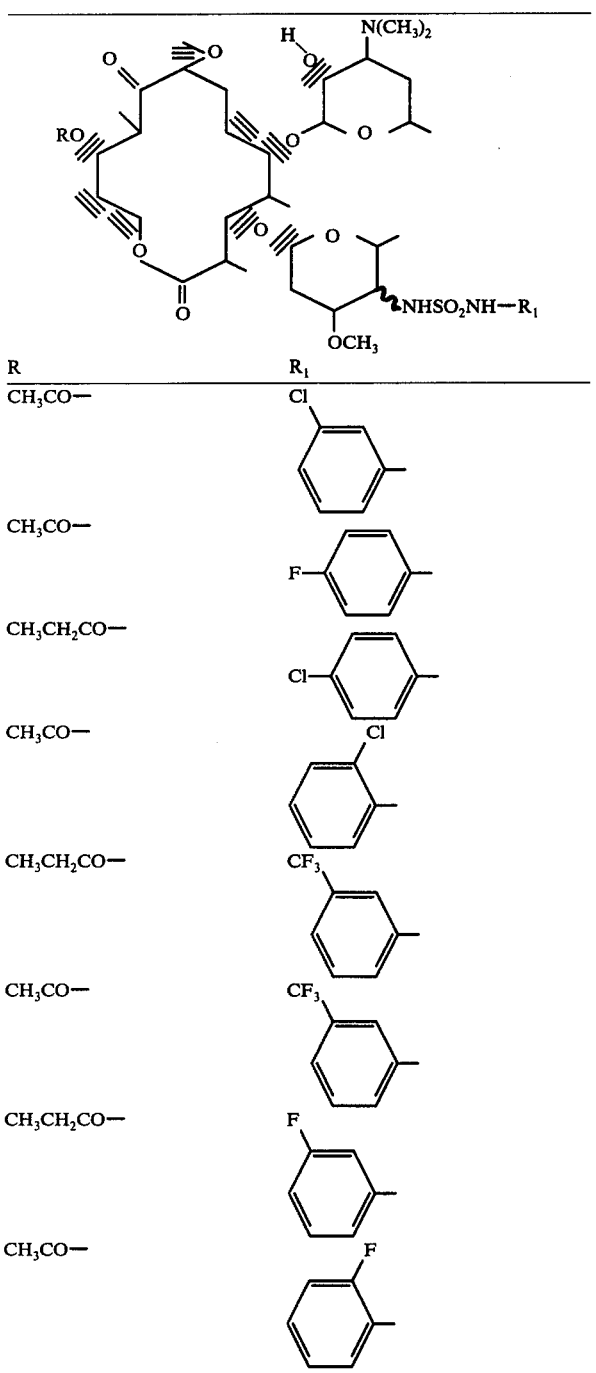

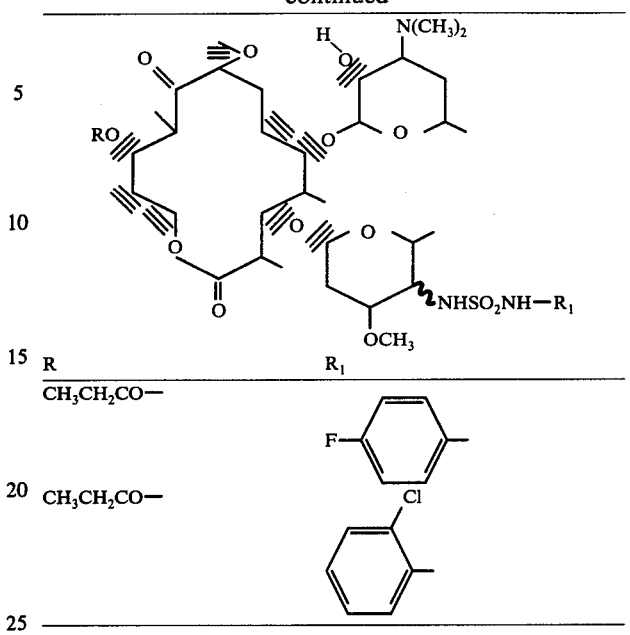

PREPARATION A

4''-Deoxy-4''-amino-oleandomycins

I. 11-Acetyl-4''-deoxy-4''-oxo-oleandomycin a. 11,2'-Diacetyl-4''-deoxy-4''-oxo-oleandomycin To a 4.5 g. of N-chlorosuccinimide, 50 ml. of benzene and 150 ml. of toluene in a dry flask fitted with a magnetic stirrer and nitrogen inlet and cooled to −5° C. is added 3.36 ml. of dimethylsulfide. After stirring at 0° C. for 20 minutes, the contents are cooled to −25° C. and treated with 5.0 g. of 11,2'-diacetyl-oleandomycin in 100 ml. of toluene. Cooling and stirring are continued for 2 hrs. followed by the addition of 4.73 ml. of triethylamine. The reaction mixture is allowed to stir at 0° C. for 15 minutes and is subsequently poured into 500 ml. of water. The pH is adjusted to 9.5 with 1N aqueous sodium hydroxide and the organic layer separated, washed with water and a brine solution and dried over sodium sulfate. Removal of the solvent in vacuo gives 4.9 g. of the desired product as a foam.

NMR (δ, CDCl₃): 3.48 (3H)s; 2.61 (2H)m; 2.23 (6H)s and 2.03 (6H)s.

b. 11-Acetyl-4''-deoxy-4''-oxo-oleandomycin

A solution of 4.0 g. of 11,2'-diacetyl-4''-deoxy-4''-oxo-oleandomycin in 75 ml. of methanol is allowed to stir at room temperature overnight. The reaction mixture is concentrated under reduced pressure to give the product as a foam. A diethyl ether solution of the residue, on treatment with hexane, gives 2.6 g. of the product as a white solid, m.p. 112°–117° C.

NMR (δ, CDCl₃): 3.43 (3H)s; 2.60 (2H)m; 2.23 (6H)s; and 2.01 (3H)s.

Similarly, by employing 11,2'-dipropionyl-4''-deoxy-4''-oxo-oleandomycin or 11-propionyl-2'-acetyl-4''-deoxy-4''-oxo-oleandomycin in the above procedure, 11-propionyl-4''-deoxy-4''-oxo-oleandomycin is prepared.

II. 11-Acetyl-4''-deoxy-4''-amino-oleandomycin

To a suspension of 10 g. of 10% palladium-on-charcoal in 100 ml. of methanol is added 21.2 g. of ammonium acetate and the resulting slurry is treated with a solution of 20 g. of 11-acetyl-4"-deoxy-4"-oxo-oleandomycin in 100 ml. of the same solvent. The suspension is shaken at room temperature in a hydrogen atmosphere at an initial pressure of 50 p.s.i. After 1.5 hrs., the catalyst is filtered and the filtrate is added with stirring to a mixture of 1200 ml. of water and 500 ml. of chloroform. The pH is adjusted from 6.4 to 4.5 and the organic layer is separated. The aqueous layer, after a further extraction with 500 ml. of chloroform, is treated with 500 ml. of ethyl acetate and the pH adjusted to 9.5 with 1N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of the purified product, m.p. 157.5°–160° C.

NMR ($\delta$, CDCl$_3$): 3.41 (3H)s; 2.70 (2H)m; 2.36 (6H)s and 2.10 (3H)s.

The other epimer, which exists in the crude foam to the extent of 20-25%, is obtained by gradual concentration and filtration of the mother liquors.

In a similar manner, starting with 11-propionyl-4"-deoxy-4"-oxooleandomycin in the above procedure, gives 11-propionyl-4"-deoxy-4"-aminooleandomycin.

What is claimed is:

1. A compound selected from the group consisting of:

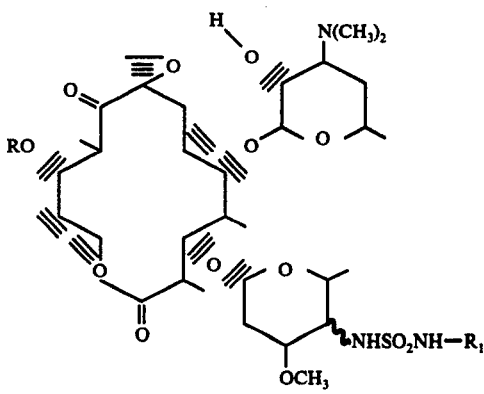

and a pharmaceutically acceptable acid addition salt thereof, wherein R is alkanoyl having two to three carbon atoms; and R$_1$ is selected from the group consisting of alkyl having from one to four carbon atoms, phenyl and substituted phenyl wherein said substituent is selected from the group consisting of methyl, methoxy, chloro, fluoro and trifluoromethyl.

2. A compound of claim 1, wherein R$_1$ is substituted phenyl wherein said substituent is selected from the group consisting of methyl, methoxy, chloro, fluoro and trifluoromethyl.

3. The compound of claim 2, N-(11-acetyl-4"-deoxy-4"-oleandomycyl)-N'-(p-methoxyphenyl)sulfamide.

4. The compound of claim 2, N-(11-acetyl-4"-deoxy-4"-oleandomycyl)-N'-(p-chlorophenyl)sulfamide.

5. The compound of claim 2, N-(11-acetyl-4"-deoxy-4"-oleandomycyl)-N'-(p-tolyl)sulfamide.

6. A compound of claim 1, wherein R$_1$ is alkyl having one to four carbon atoms.

7. The compound of claim 6, N-(11-acetyl-4"-deoxy-4"-oleandomycyl)-N'-methylsulfamide.

* * * * *